United States Patent [19]

Batcho et al.

[11] 4,360,470

[45] Nov. 23, 1982

[54] PROCESS AND INTERMEDIATES FOR THE SYNTHESIS OF VITAMIN $D_3$ METABOLITES AND CHENODEOXYCHOLIC ACID

[75] Inventors: Andrew D. Batcho, North Caldwell; Milan R. Uskokovic, Upper Montclair; Peter M. Wovkulich, Nutley, all of N.J.

[73] Assignee: Hoffmann-La Roche Inc., Nutley, N.J.

[21] Appl. No.: 199,168

[22] Filed: Oct. 22, 1980

[51] Int. Cl.[3] .................................................. C07J 9/00
[52] U.S. Cl. .............................. 260/397.1; 260/397.2; 260/397.5
[58] Field of Search ........................... 260/397.1, 397.5

[56] References Cited

U.S. PATENT DOCUMENTS 4,269,777  5/1981  De Luca et al. .......... 260/239.55 D

OTHER PUBLICATIONS

Chem. Abstracts vol. 81 (1974) pars. 25,848T.

*Primary Examiner*—Elbert L. Roberts
*Attorney, Agent, or Firm*—Jon S. Saxe; Bernard S. Leon; James H. Callwood

[57] ABSTRACT

The present disclosure is directed to a process for the synthesis of chenodeoxychloic acid, 25-hydroxycholesterol and $1\alpha,25$-dihydroxycholesterol from 17-keto steroids. A cholic acid side chain is stereospecifically introduced by reaction of the appropriate 17-keto steroid with ethyltriphenylphosphonium halides to produce the 17-ethylidene derivative which is allowed to react with acrylic acid esters or propiolic acid esters followed by hydrogenation.

43 Claims, No Drawings

PROCESS AND INTERMEDIATES FOR THE SYNTHESIS OF VITAMIN D₃ METABOLITES AND CHENODEOXYCHOLIC ACID

BACKGROUND OF THE INVENTION

The preparation of steroids such as chenodeoxycholic acid, 25-hydroxycholesterol and 1α,25-dihydroxycholesterol, the last two compounds being useful intermediates for the preparation of Vitamin D₃ metabolites, has involved numerous problems. For example, in the past, it has been necessary to utilize procedures involving many preparative steps, thereby resulting in low overall yields of the ultimate product. Additionally, the synthetic procedures have been time-consuming and tedious, involving the need for separation of various products by chromatographic procedures in order to arrive at a substrate having the natural steroid configuration at the 20-position. Because of the foregoing problems, it has heretofore been impractical to prepare these compounds of potential commercial importance on a commercially-practical scale.

17-keto steroids, such as dehydroepiandrosterone, are available from microbial degradation of readily-available plant steroids such as sitosterol, campesterol, etc. Thus, the 17-keto steroids are abundantly-available substrates which could provide attractive starting materials for the synthesis of a number of steroid compounds which are of potential, commercial importance. For example, 17-keto steroids can be hydroxylated microbially, thereby eliminating time-consuming preparative steps which are normally associated with the construction of a suitable substrate. However, there has heretofore been no methodology available for the efficient stereospecific introduction of a side chain at the 17-position having the natural steroid C-20 configuration which would allow for further elaboration of these substrates into commercially-important products.

The ene reaction, which is known in the prior art, involves the addition of a compound with a double bond (enophile) to an olefin possessing an allylic hydrogen (ene) and involves allylic shift of the double bond, transfer of the allylic hydrogen to the enophile and bonding between the two unsaturated termini. It is also known in the prior art that 17-keto steroids may be modified by reaction with an ethyltriphenylphosphonium halide to produce 17-ethylidene derivatives having a Z-double bond configuration.

SUMMARY OF THE INVENTION

In accordance with the present invention, it has been found that chenodeoxycholic acid can be prepared from the 3α,7α-dihydroxy-17-keto steroid characterized by the formula

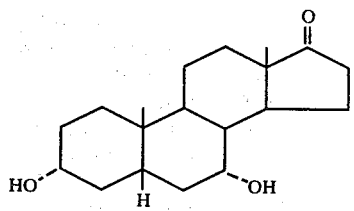

by reaction with an ethyltriphenylphosphonium halide via a Wittig reaction so as to produce an ethylidene derivative of the formula

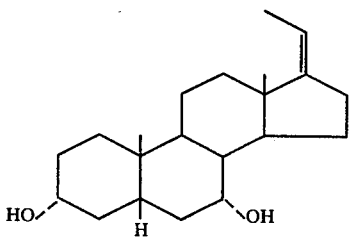

The compound of formula I is then reacted with an acylating agent so as to produce a compound of the formula

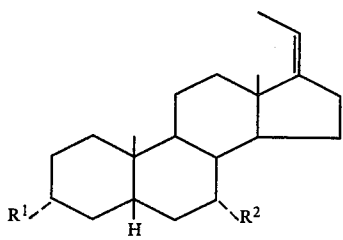

wherein $R^1$ and $R^2$ are acyloxy, followed by transformation via an ene reaction with acrylic acid esters to stereoselectively produce a compound of the formula

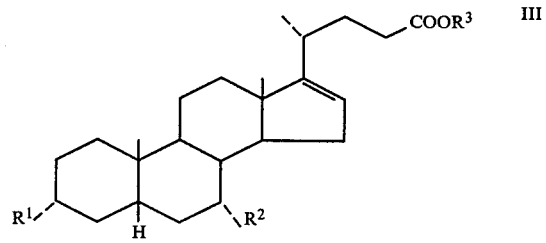

wherein $R^1$ and $R^2$ are as above; and $R^3$ is lower alkyl, followed by hydrogenation of the Δ¹⁶ double bond to produce a compound of the formula

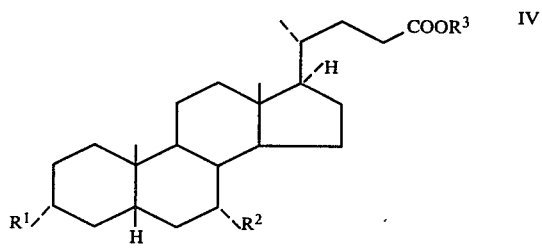

wherein $R^1$, $R^2$ and $R^3$ are as above, followed by saponification by known procedures with aqueous base to yield chenodeoxycholic acid as characterized by the formula

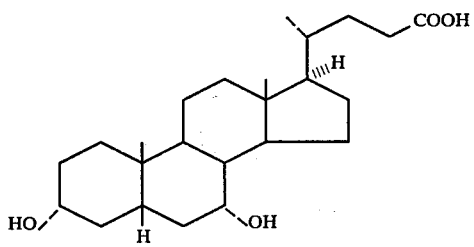

In an alternative embodiment of the present invention, it has been found that 17-keto steroids once they have been reacted with an ethyltriphenylphosphonium halide via a Wittig reaction to produce ethylidene derivatives of the formula

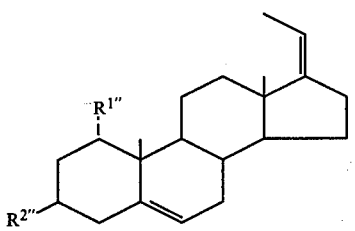

wherein $R^{1''}$ is hydrogen, hydroxy or acyloxy; and $R^{2''}$ is hydroxy or acyloxy, can be transformed via an ene reaction with acrylic acid esters, stereospecifically in respect to the C-20 configuration, so as to produce a compound of the formula

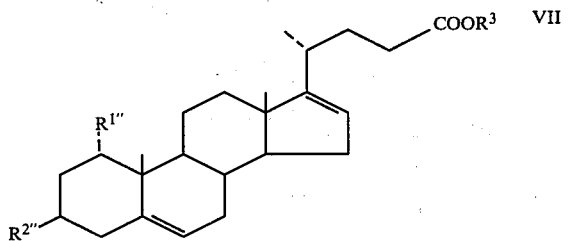

wherein $R^{1''}$ is hydrogen, hydroxy or acyloxy; $R^{2''}$ is hydroxy or acyloxy; and $R^3$ is lower alkyl, followed by selective hydrogenation of the $\Delta^{16}$ double bond so as to produce a compound of the formula

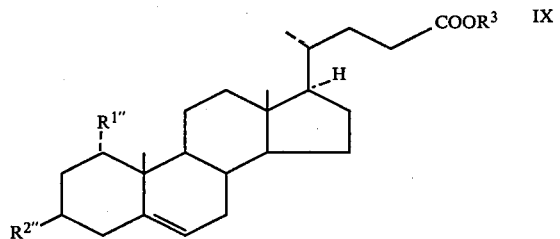

wherein $R^{1''}$, $R^{2''}$ and $R^3$ are as above.

Or, alternatively, the compound of formula VI may be reacted with propiolic acid esters so as to produce a compound of the formula

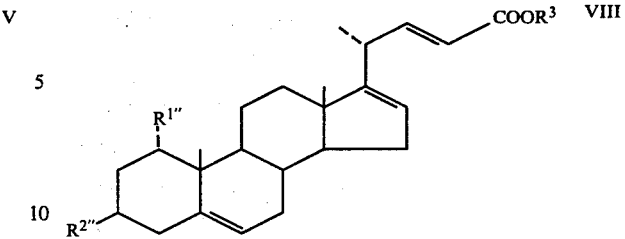

wherein $R^{1''}$, $R^{2''}$ and $R^3$ are as above, followed by selective hydrogenation of the $\Delta^{16}$ and $\Delta^{22}$ double bonds so as to produce compounds of the formula

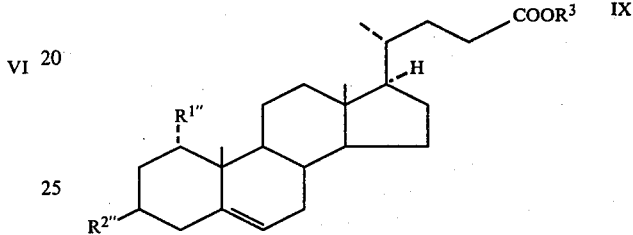

wherein $R^{1''}$, $R^{2''}$ and $R^3$ are as above.

The compounds of formula IX are then subjected to reaction conditions and procedures well known in the art to produce 1α,25-dihydroxycholesterol.

DETAILED DESCRIPTION OF THE INVENTION

As used throughout the specification and the appended claims, the term "lower alkyl" means straight- or branched-chain saturated aliphatic hydrocarbon groups preferably containing 1–7 carbon atoms. Representative of such groups are methyl, ethyl, isopropyl, butyl, pentyl hexyl, heptyl and octyl. The term "acyloxy" means the residue of an alkyl or aromatic carboxylic acid formed by the removal of a hydrogen atom from the hydroxyl portion of the carboxyl group. Examples of such acids are formic acid, acetic acid, pivalic acid, propionic acid, butyric acid, caproic acid, oenanthic acid, undecylenic acid and oleic acid. Preferred acyloxy groups are $C_{1-7}$ alkanoyloxy groups, especially acetyloxy. Acetyloxy may be substituted, for example, trihaloacetyloxy. Aromatic acyloxy groups are the residue of organic carboxylic acid containing 7–15 carbon atoms such as benzoic acid, phenylacetic acid and the like. The term "aryl" means an organic, aromatic radical derived by the removal of one atom (e.g., phenyl) which can be unsubstituted or substituted by one or more lower alkyl groups (e.g., tolyl).

In the formulas represented herein, the various substituents are illustrated as joined to the steroid nucleus by one of the following notations:

A solid line (—) indicates that a substituent is in the β-orientation (i.e., above the plane of the molecule) and a broken line (---) indicates that a substituent is in the α-orientation (i.e., below the plane of the molecule).

In the first step of the process of the present invention for the preparation of chenodeoxycholic acid, the 3α,-7α-dihydroxy-17-keto steroid characterized by the formula

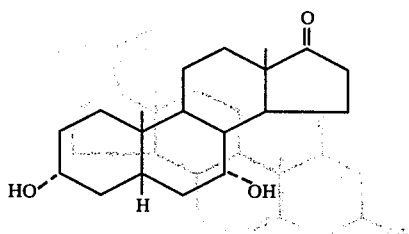

XI is reacted with an ethyltriphenylphosphonium halide via a Wittig reaction in the presence of strong base so as to produce a compound of the formula

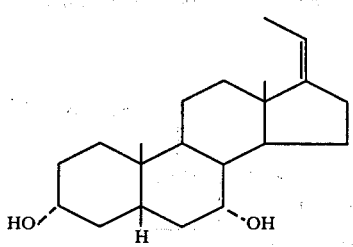

I

The reaction is carried out in an inert organic solvent under an inert atmosphere at reaction temperatures ranging from 0° to 150° C. The inert organic solvents which may be used in the present process may be any inert organic solvent as exemplified by tetrahydrofuran, dimethylsulfoxide, dimethylformamide, benzene, toluene, hexane and the like. The strong base which may be used is any strong base conventionally known in the art capable of forming a Wittig reagent from an ethyltriphenylphosphonium halide. Exemplary of such strong bases are lower alkyl alkali metal salts, for example, butyllithium, alcohol salts such as potassium tertiary butylate, potassium amylate and the like.

The reaction temperature at which the foregoing reaction can be carried out is not critical and can range from 0° to 150° C. with room temperature being preferred.

The compound of formula I is then reacted with an acylating agent so as to produce a compound of the formula

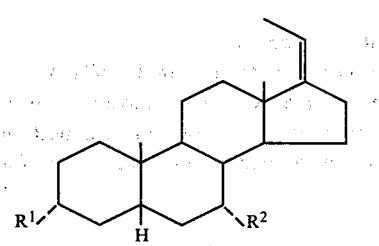

II wherein $R^1$ and $R^2$ are acyloxy.

Exemplary of suitable acylating agents are lower alkyl carboxylic acid anhydrides, for example, acetic anhydride; aromatic anhydride, for example, benzoic anhydride, nitrobenzoic anhydride, toluic anhydride and the like. The acylating agent is added in the presence of a weak base such as pyridine, dimethylaniline, triethylamine, sodium acetate and the like at temperatures ranging from 0°–150° C., preferably 60°–90° C.

In the second and key step of the process of the present invention for the preparation of chenodeoxycholic acid, the compound of formula II is allowed to react with an acrylic acid ester in the presence of a Lewis acid catalyst such as ethylaluminum dichloride via the ene reaction so as to produce a compound of the formula

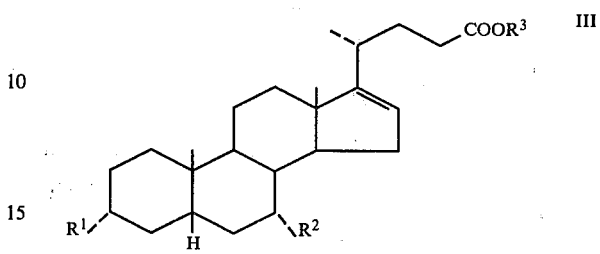

III wherein $R^1$ and $R^2$ are as above; and $R^3$ is lower alkyl.

This reaction may be carried out in any conventional inert solvent, for example, methylene chloride, carbon tetrachloride, chloroform, aromatic hydrocarbons such as benzene, toluene and the like, and lower aliphatic hydrocarbons such as hexane, octane and the like. The reaction is carried out at temperatures ranging from −20° to 45° C., the particular reaction temperature not being critical. The reaction is catalyzed by Lewis acid catalysts such as lower alkyl aluminum dihalides and aluminum trihalides in weak base. Exemplary of such catalysts are ethylaluminum dichloride, aluminum tribromide with pyridine or aluminum chloride with pyridine with aluminum chloride and pyridine being preferred.

The compound of formula III is reacted in a hydrogen atmosphere in the presence of a conventional hydrogenation catalyst thereby reducing the $\Delta^{16}$ double bond so as to produce a compound of the formula

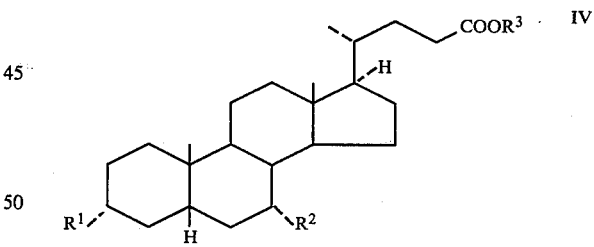

IV wherein $R^1$, $R^2$ and $R^3$ are as above.

Exemplary of suitable hydrogenation catalysts are platinum on charcoal, platinum oxide, Raney nickel and palladium on charcoal.

The $3\alpha,7\alpha$-diacetyloxy-$5\beta$-cholan-24-oic acid ester compound of formula IV can be converted to chenodeoxycholic acid by reacting the compound of formula IV with aqueous base such as potassium hydroxide at temperatures ranging from room temperature to reflux temperature to saponify the acyl groups at the 1- and 7-positions and to cleave the ester group at the 24-position resulting in chenodeoxycholic acid characterized by the formula

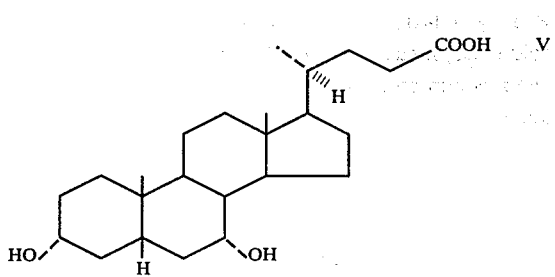

V

The reaction is carried out under conditions well known in the art, for example, at temperatures ranging from room temperature to reflux temperature.

In an alternative embodiment, 25-hydroxycholesterol and 1α,25-dihydroxycholesterol may be prepared according to the process of the present invention by reacting 17-keto steroids of the formula

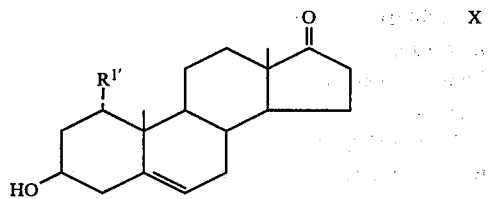

X wherein $R^{1'}$ is hydrogen or hydroxy,
with an ethyltriphenylphosphonium halide via a Wittig reaction in the presence of strong base so as to produce a compound of the formula.

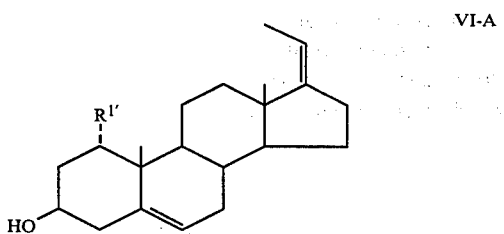

VI-A wherein $R^{1'}$ is as above.

The reaction is carried out in an inert organic solvent under an inert atmosphere at reaction temperatures ranging from 0° to 150° C. The inert organic solvents which may be used in the present process may be any inert organic solvent. Exemplary of such solvents are tetrahydrofuran, dimethylsulfoxide, dimethylformamide, benzene, toluene, hexane and the like. The strong base which may be used is any strong base conventionally known in the art capable of forming a Wittig reagent from an ethyltriphenylphosphonium halide. Exemplary of such strong bases are lower alkyl alkali metal salts, for example, butyllithium, alcohol salts such as potassium tertiary butylate, potassium amylate and the like.

The reaction temperature at which the foregoing reaction can be carried out is not critical and can range from 0° to 150° C. with room temperature being preferred.

The compound of formula

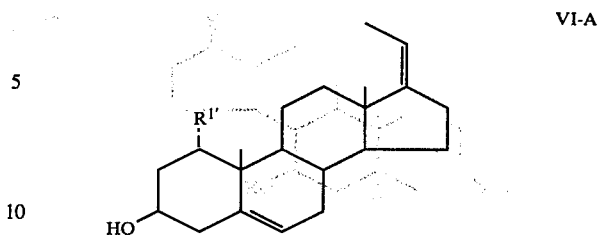

VI-A wherein $R^{1'}$ is hydrogen or hydroxy,
is allowed to react with an acrylic acid ester under conditions hereinafter described to yield a compound of the formula

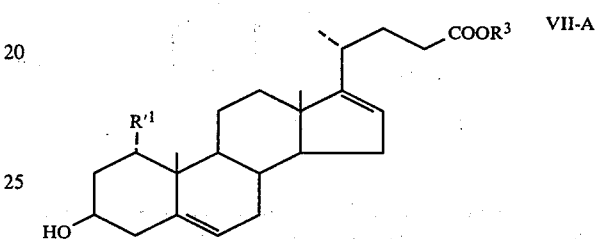

VII-A wherein $R^{1'}$ is hydrogen or hydroxy; and $R^3$ is lower alkyl.

Or, alternatively, the compound of formula VI-A is allowed to react with a propiolic acid ester under conditions hereinafter described to yield a compound of the formula

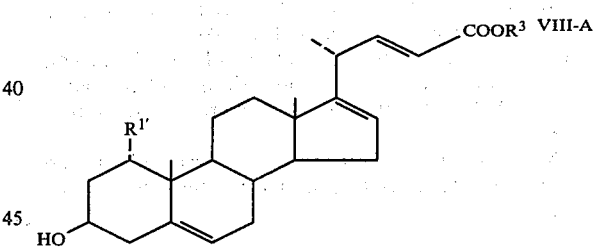

VIII-A wherein $R^{1'}$ is as above.

The reaction products of formulas VII-A or VIII-A are then reacted in a hydrogen atmosphere in the presence of a hydrogenation catalyst under conditions hereinafter described to yield a compound of the formula

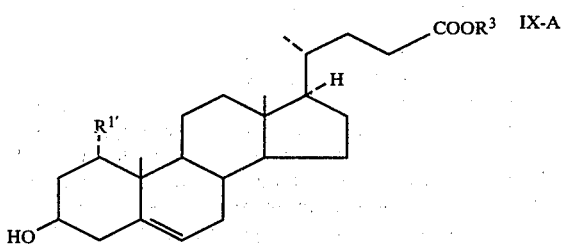

IX-A wherein $R^{1'}$ and $R^3$ are as above.

If it is desired to produce the compound of formula VI-B

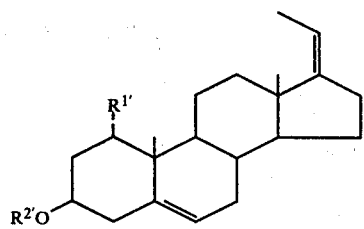

VI-B wherein R$^{1\prime}$ is hydrogen or hydroxy; and R$^{2\prime}$ is acyl, the compound of formula VI-B is reacted with 1 mole of an acylating agent. One mole of an acylating agent will selectively acylate the hydroxy group at position 3.

If it is desired to produce a compound of formula VI-C

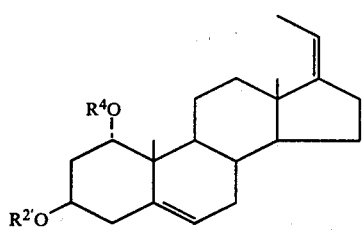

VI-C wherein R$^{2\prime}$ and R$^4$ are both acyl, the compound of formula VI-A, wherein R$^{1\prime}$ is hydroxy, is reacted with 2 moles of an acylating agent so as to acylate the hydroxy groups at the 1- and 3-positions. When 2 moles of an acylating agent are reacted with a compound having hydroxy groups at the 1- and 3-positions, both hydroxy groups are converted to acyloxy groups.

Exemplary of suitable acylating agents are lower alkyl carboxylic acid anhydrides, for example, acetic anhydride and trifluoroacetic anhydride; aromatic anhydrides, for example, benzoic anhydride, nitrobenzoic anhydride, toluic anhydride and the like. The acylating agent is added in the presence of a weak base such as pyridine, dimethylaniline, triethylamine, sodium acetate and the like. Dimethylaminopyridine may optionally be added to catalyze the reaction.

If it is desired to produce a compound of the formula

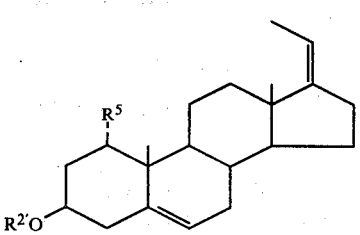

VI-D wherein R$^{2\prime}$ is hydrogen; and R$^5$ is acyloxy, the compound of formula VI-C may be reacted with 1 mole of a base at reflux conditions. The acyl group R$^{2\prime}$ will be hydrolyzed, thereby selectively removing the acyl protecting group at the 3-position.

In the second and key step of the alternative aspect of the present invention, the compound of formula VI

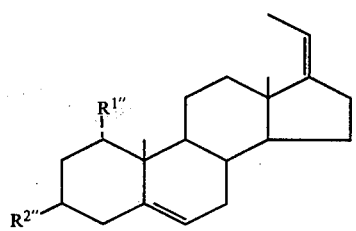

VI wherein R$^{1\prime\prime}$ is hydrogen, hydroxy or acyloxy; and R$^{2\prime\prime}$ is hydroxy or acyloxy, is allowed to react with an acrylic acid ester via the ene reaction so as to produce a compound of the formula

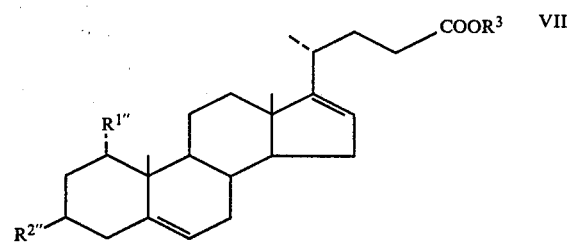

VII wherein R$^{1\prime\prime}$ and R$^{2\prime\prime}$ are as above; and R$^3$ is lower alkyl.

This reaction is carried out in any conventional inert solvent; for example, methylene chloride, carbon tetrachloride, chloroform, aromatic hydrocarbons such as benzene, toluene and the like, and lower aliphatic hydrocarbons such as hexane, octane and the like. The reaction may also be carried out in aqueous systems using protic acids. The reaction is carried out at temperatures ranging from $-20°$ to $45°$ C., the particular reaction temperature not being critical. The reaction is catalyzed by Lewis acids such as lower alkyl aluminum dihalides and aluminum trihalides in weak base as exemplified by ethylaluminum dichloride, aluminum tribromide with pyridine and aluminum chloride with pyridine.

The compound of formula VII is reacted in a hydrogen atmosphere in the presence of a hydrogenation catalyst thereby selectively hydrogenating the $\Delta^{16}$ double bond so as to produce a compound of the formula

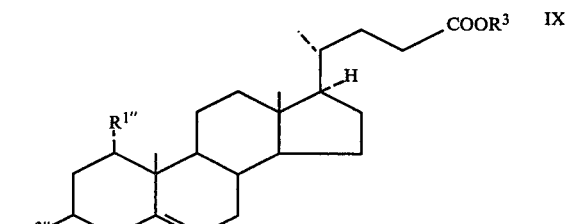

IX wherein R$^{1\prime\prime}$, R$^{2\prime\prime}$ and R$^3$ are as above.

Preferred hydrogenation catalysts are platinum on charcoal, platinum oxide and Raney nickel. The reaction is carried out in an inert solvent under a hydrogen atmosphere at temperatures ranging from $0°$ to $40°$ C., preferably $23°$ C.

In an alternative embodiment, the compound of formula VI may be reacted with propiolic acid ester under conditions previously defined so as to produce a compound of the formula

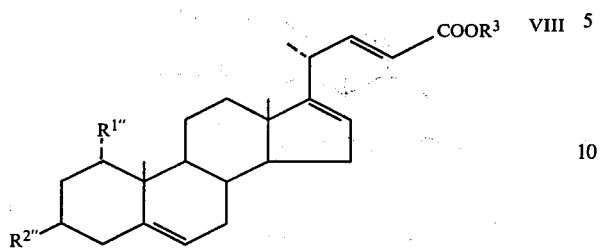

wherein $R^{1''}$, $R^{2''}$ and $R^3$ are as above.

The compounds of formulas VII or VIII are then reacted with hydrogen in the presence of a hydrogenation catalyst to selectively reduce the $\Delta^{16}$ double bond in the compound of formula VII and the $\Delta^{16}$ and $\Delta^{22}$ double bonds in the compound of formula VIII so as to produce a compound of the formula

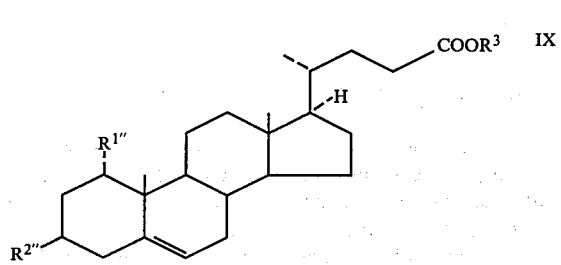

wherein $R^{1''}$ and $R^{2''}$ are as above.

The compound of formula IX has the natural steroid stereochemistry at the 20-position and is a suitable substrate for further conversion to 25-hydroxycholesterol and 1α,25-dihydroxycholesterol. For example, the compound of formula IX can be reacted with diisobutylaluminum hydride under an inert atmosphere in an inert organic solvent so as to produce a compound of the formula

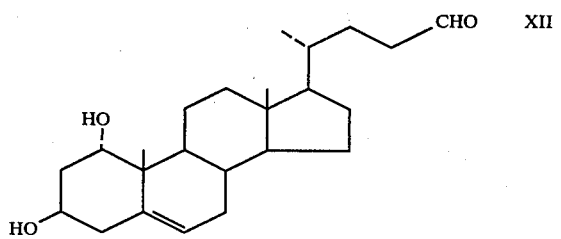

The foregoing reaction can be carried out at temperatures ranging from $-40°$ to $-80°$ C., preferably $-60°$ to $-80°$ C.

The compound of formula XII is in turn reacted with potassium tertiary-butoxide and isopropyltriphenylphosphonium bromide in an inert organic solvent at temperatures ranging from $-70°$ to 100° C. so as to produce a compound of the formula

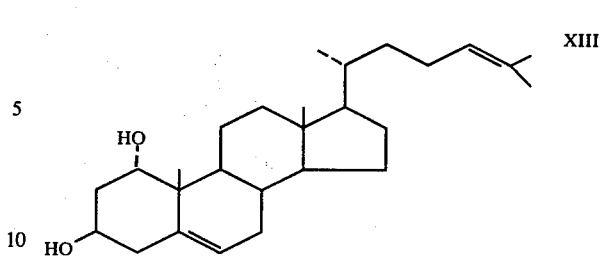

The compound of formula XIII is in turn reacted with mercuric acetate in the presence of sodium borohydride to yield 1α,25-dihydroxycholesterol characterized by the formula

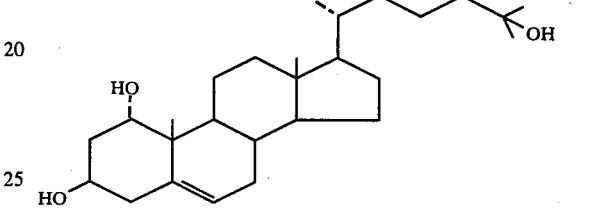

The foregoing invention can be better understood by reference to the following examples:

EXAMPLE 1

Preparation of (Z)-3α,5β,7α-Pregn-17(20)-ene-3,7-diol

A solution of 1.282 g (ca. 0.0034 mol) of 3α,5β,7α-3,7-dihydroxyandrostan-17-one in 5 ml of tetrahydrofuran was added to a room temperature solution of 113 ml of tetrahydrofuran, 1.875 g (0.0167 mol) of potassium t-butoxide and 6.215 g (0.0167 mol) of ethyltriphenylphosphonium bromide. The mixture was stirred under argon for 72 hr. and then was poured into 750 ml of water containing 250 g of ice. After 30 min., the mixture was collected by suction filtration and washed with water. The dried, crude material (3.0 g) was chromatographed on 200 g of silica gel to afford, on elution with ethyl acetate—hexane (2:1), 0.888 g of material (82%). Trace amounts of impurities were removed by dissolving in a mixture of hexane and methylene chloride. The methylene chloride was distilled, the mixture was cooled, and the solid product, (Z)-3α,5β,7α-pregn-17(20)-ene-3,7-diol, was collected by filtration. The analytical sample was recrystallized from ethyl acetate then acetonitrile, mp 160°–161° C.

EXAMPLE 2

Preparation of (Z)-3α,5β,7α-Pregn-17(20)-ene-3,7-diol Diacetate

To a solution of 0.60 g (0.00188 mol) of (Z)-3α,5β,7α-pregn-17(20)-ene-3,7-diol and 30 ml of dry toluene was added 1.8 ml (ca. 1.84 g=0.023 mol) of dry pyridine, 1.8 ml (ca. 1.66 g=0.016 mol) of acetic anhydride and 0.016 g (0.00013 mol) of 4-dimethylaminopyridine. The mixture was stirred under argon atmosphere for 18 hr. and then poured into 100 ml of water, acidified with 1 N HCl and extracted with 3×50 ml of ethyl acetate. The combined organic phases were washed with water until neutral and then dried over anhydrous sodium sulfate. Filtration and evaporation of the solvent in vacuo gave 0.789 g of crude product. TLC revealed an incomplete reaction so the above procedure was repeated. The product was recrystallized from methanol to afford 0.566 g (75%) of (Z)-3α,5β,7α-pregn-17(20)-ene-3,7-diol diacetate. The analytical sample, recrystallized twice from methanol, had mp 92°-93° C.

EXAMPLE 3

Preparation of 3α,5β,7α-3,7-Diacetyloxychol-16-en-24-oic Acid Methyl Ester

In a dry, round-bottom flask with magnetic stirrer, argon atmosphere and rubber septum was placed 3 ml of dry (4 Å molecular sieves) methylene chloride, 0.108 ml (0.00131 mol) of methyl acrylate and 1.092 ml (0.00161 mol) of ethylaluminum dichloride in hexane (25%). At 0° C., 0.220 g (0.00055 mol) of (Z)-3α,5β,7α-pregn-17(20)-3,7-diol diacetate in 1 ml of dry methylene chloride was added via syringe. The cooling bath was removed, and the mixture was stirred for 72 hr. The cloudy mixture was quenched by the addition of 5 ml of a 30% (by weight) solution of potassium sodium tartrate. The mixture was transferred to a separatory funnel containing 50 ml of 15% potassium sodium tartrate and extracted with 4×25 ml of methylene chloride. The combined organic extracts were washed with water, then brine, and dried over anhydrous sodium sulfate. Filtration of the solution and removal of solvent in vacuo gave 0.277 g of crude product which was chromatographed on 30 g of silica gel 60. Elution with hexane—ethyl acetate (3:1) afforded 0.162 g (72%) of 3α,5β,7α-3,7-diacetyloxychol-16-en-24-oic acid methyl ester. An analytically-pure sample, obtained by chromatographing the product mixtures from several similar experiments on silica gel 60 (200-400 mesh), eluting with hexane—methylene chloride—ethyl acetate (9:9:2) and then recrystallization from hexane—ethyl acetate, had mp 109°-110° C.

EXAMPLE 4

Preparation of methyl 3α,7α-diacetyloxy-5β-cholan-24-oate

A mixture of 0.150 g (0.000307 mol) of 3α,5β,7α-3,7-diacetyloxychol-16-en-24-oic acid methyl ester, 10 ml of isopropanol and 0.050 g of 5% palladium on carbon catalyst was stirred under an atmosphere of hydrogen for 20 hr. The mixture was filtered through Celite and the solvent removed in vacuo to give 0.171 g of crude product. Chromatography on silica gel 60 (200-400 mesh), eluting with hexane—methylene chloride—ethyl acetate (9:9:2), gave 0.112 g (73%) of methyl 3α,7α-diacetyloxy-5β-cholan-24-oate. Recrystallization from methanol afforded crystals of mp 129.5°-130° C. which did not depress on mixture with authentic material prepared from chenodeoxycholic acid.

EXAMPLE 5

Preparation of Chenodeoxycholic Acid

To a solution of 3 ml of methanol, 5 ml of isopropanol and 0.8 g of potassium hydroxide was added 0.294 g (0.000599 mol) of methyl 3α,7α-diacetyloxy-5β-cholan-24-oate. The mixture was heated to reflux under an argon atmosphere for 4 hr. then stirred overnight at room temperature. The solvents were removed in vacuo. The mixture was acidified with 1 N HCl and extracted with 3×25 ml of ethyl acetate. The combined ethyl acetate extracts were washed with water then dried over anhydrous sodium sulfate. The mixture was filtered and solvents removed in vacuo. The residue were recrystallized from ethyl acetate to give 0.163 g (69.3%) of chenodeoxycholic acid, mp 117°-118° C., which did not depress when mixed with authentic material (mp 117°-118° C. from ethyl acetate).

EXAMPLE 6

Preparation of 1α,3β-Diacetyloxychola-5,16-dien-24-oic Acid Methyl Ester

To a stirred solution of 4.5 ml (50 mmol) of methyl acrylate in 230 of dry methylene chloride (over 4 Å molecular sieves) under a nitrogen atmosphere cooled to 5° in an ice bath was added 65 ml of 25% (98 mmol) ethylaluminum dichloride in hexane. Immediately thereafter was added 10.0 g (25 mmol) of (Z)-Pregna-5,17(20)-diene-1α,3β-diol diacetate. The light, amber-colored solution was allowed to come to room temperature (bath removed) and left stirring overnight (23 hr). An additional 2.5 ml (28 mmol) of methyl acrylate was added, followed by 12 ml (18 mmol) of 25% ethylaluminum dichloride in hexane. After stirring overnight, the reaction mixture was cautiously poured into a vigorously-stirred, ice-cold 100 ml of saturated sodium dihydrogen phosphate. The suspension was acidified while cold with 250 ml of 2 N hydrochloric acid and extracted with 2×250 ml methylene chloride. The organic phases were washed with 250 ml of 10% sodium bicarbonate solution. After filtration through a bed of diatomaceous earth (to remove a gelatinous precipitate), the phases were separated. The diatomaceous earth bed was washed several times with methylene chloride. The combined methylene chloride extracts (from the aqueous and diatomaceous earth extractions) were dried ($Na_2SO_4$), filtered and evaporated to give 12.4 g of amorphous residue. High-pressure liquid chromatography on 1 kg of silica gel, using 10:1 hexane—ethyl acetate as eluting solvent, afforded, in fractions 11-22, combined according tlc (3:1, hexane—EtOAc), 9.2 g (76%) of amorphous 1α,3β-diacetoxyloxychola-5,16-dien-24-oic acid methyl ester.

EXAMPLE 7

Preparation of 1α,3β-Diacetyloxychol-5-en-24-oic Acid Methyl Ester

To a solution of 8.8 g of 1α,3β-diacetyloxychola-5,16-dien-24-oic acid methyl ester in 200 ml of absolute ethanol was added, under a nitrogen atmosphere, 0.8 g of 5% platinum on charcoal. The suspension was then stirred under a hydrogen atmosphere at 23° C. until hydrogen absorption ceased (2.75 h; 423 ml; theory, 437 ml). Filtration through diatomaceous earth did not remove all colloidal particles. The evaporated filtrate was dissolved in 50 ml of ethyl acetate—methylene chloride (1:1) and was then percolated through a column of 20 g of silica gel using the same solvent mixture. Evaporation of the solvents gave 8.7 g (99%) of 1α,3β-diacetyloxychol-5-en-24-oic acid methyl ester as a white solid, mp 108°-113° C. An analytical sample, recrystallized from methanol, had mp 110.5°-112° C.

EXAMPLE 8

Preparation of 1α,3β-Dihydroxychol-5-en-24-al

To a stirred solution of 978 mg (2.0 mmol) of 1α,3β-diacetyloxychol-5-en-24-oic acid methyl ester in 20 ml of methylene chloride cooled to −70° (dry ice-acetone bath) under a nitrogen atmosphere was added dropwise (15 min.), maintaining the temperature between −60° and −70°, 8 ml (12 mmol) of 1.5 M diisobutylaluminum hydride in toluene. The resulting paste was stirred for an additional 15 min. before adding successively 2 ml of methanol and 4 ml of water. The bath was removed, the reaction mixture allowed to reach room temperature and 9 g of potassium sodium tartrate salts and 20 ml of water were added; the suspension was extracted with 2×50 ml of methylene chloride which were back-washed in a countercurrent manner with a solution of 20 ml of water and 9 g of potassium sodium tartrate salts. After drying (Na$_2$SO$_4$), filtering and evaporating, 782 mg of amorphous solid was obtained. Chromatography on 40 g of silica gel prepared in and eluted with ethyl acetate gave, in fraction 11–20 (10 ml fractions), 543 mg of amorphous solid. Fractions 21–100 (188 mg) were rechromatographed in a similar manner to yield an additional 71 mg of product. Thus, a total of 614 mg (82%) of 1α,3β-dihydroxychol-5-en-24-al was obtained. An analytical sample crystallized from acetonitrile had mp 120°–122° C.

EXAMPLE 9

Preparation of 1α,3β-Cholesta-5,24-diene-1,3-diol

To a stirred suspension of 2.3 g (6.0 mmol) of isopropyltriphenylphosphonium bromide in 10 ml of THF under a nitrogen atmosphere was added 673 mg (6.0 mmol) of potassium tert.-butoxide. To the blood-red suspension was added over 10 min., a solution of 1.124 g (3.0 mmol) of 1α,3β-dihydroxychol-5-en-24-al in 20 ml of THF. The red color persisted. After 2 hr., 10 ml of acetic anhydride followed by 10 ml of pyridine and 61 mg of 4-dimethylaminopyridine was added (color immediately discharged). The suspension was heated in a 100° oil bath, and the THF was allowed to slowly distill until the pot temperature reached 98° (ca. 1 hr.). After a total of 2 hr. of heating, the dark amber solution was allowed to cool overnight. After addition of 25 ml of water and 25 ml of methanol, the suspension was extracted with 3×100 ml of hexane, the hexane phases were washed in a countercurrent manner with 50 ml of methanol-water (1:1), 2×50 ml of 1 N hydrochloric acid and 50 ml of 10% sodium bicarbonate. After drying (Na$_2$SO$_4$), filtering and evaporation of the solvent, 1.60 g of amber oil remained. Chromatography on 60 g of silica gel prepared in hexane and eluted with 12:1 hexane—ethyl acetate afforded, in fractions 22–40 (10 ml fractions), 1.284 g (88%) of 1α,3β-cholesta-5,24-diene-1,3-diol diacetate. An analytical sample crystallized from methanol had mp 133°–134.5° C.

The crude diacetate was saponified by heating at reflux in methanol in hydroxide solution for 1 hr. After evaporation of the methanol, the residue was taken up with water and extracted with ethyl acetate. The organic phase was dried (Na$_2$SO$_4$), filtered and evaporated to give 1α,3β-cholesta-5,24-diene-1,3-diol. An analytical sample crystallized from ethanol had mp 137°–139° C.

EXAMPLE 10

Preparation of 1α,25-Dihydroxycholesterol

To a cooled, stirred solution of 4.05 g (10.1 mmol) of cholesta-5,24-diene-1α,3β-diol in 53 ml of tetrahydrofuran in an ice bath was added 33 ml of water followed by 4.0 g (12.5 mmol) of mercuric acetate. The bath was removed. After 2 hr., the reaction was still incomplete (tlc) so 0.4 g (1.3 mmol) of mercuric acetate was added. After 4 hr., 800 mg (21.1 mol) of sodium borohydride was added, followed after 30 min. by 190 ml of saturated brine and extraction of the resulting suspension with 5×50 ml of methylene chloride. The organic phases were backwashed with 20 ml of brine, dried (Na$_2$SO$_4$), filtered and evaporated. The residue was chromatographed on 400 g of silica gel. Elution with 5% methanol—chloroform and combination of fractions according to tlc (10% methanol—chloroform) afforded 3.60 g (85%) of 1α,25-dihydroxycholesterol, mp 165°–167° C.

EXAMPLE 11

Preparation of 1α,3β-Diacetyloxychola-5,16,22-trien-24-oic Acid Methyl Ester

To a magnetically-stirred solution of 3.9 ml (45 mmol) of methyl propiolate and 150 ml of dry methylene chloride under an argon atmosphere was added by syringe 58 ml (107 mmol) of 25% ethylaluminum dichloride in toluene, followed as rapidly as possible by a solution of 12.0 g (30 mmol) of Z-pregna-5,17(20)-diene-1α,3β-diol diacetate in 150 ml of dry methylene chloride. The temperature rose to 35° after the catalyst addition. After 1.75 hr., the yellow reaction solution was poured into a well-stirred, ice-cold 1 l. of saturated sodium dihydrogen phosphate solution. About 600 ml of ethyl acetate was added, and the phases were separated. The aqueous phase was extracted with 2×600 ml of ethyl acetate, and the organic phases were washed in a countercurrent manner with 500 ml of water and 500 ml of brine, dried (Na$_2$SO$_4$), filtered and evaporated to give 15.32 g of crude product. High-pressure liquid chromatography on 1 kg of silica gel using 9:1 hexane—ethyl acetate for elution afforded after three passes 12.9 g (89%) of 1α,3β-diacetyloxychola-5,16,22-trien-24-oic acid methyl ester as an amorphous solid.

EXAMPLE 12

Preparation of 1α,3β-Diacetyloxychol-5-en-24-oic Acid Methyl Ester

To a solution (under a nitrogen atmosphere) of 485 mg (1 mmol) of 1α,3β-diacetyloxychola-5,16,22-trien-24-oic acid methyl ester in 25 ml of ethyl acetate was added 50 mg of 5% platinum on charcoal. The suspension was stirred under a hydrogen atmosphere until hydrogen uptake ceased (2.25 h; 49.9 ml; theory, 48.6 ml). The catalyst was removed by filtration through a bed of diatomaceous earth which was washed several times with methylene chloride. Evaporation of the filtrate gave 492 mg of crystalline product which was recrystallized from 5 ml of methanol to give 358 mg (73%) of 1α,3β-diacetyloxychol-5-en-24-oic acid methyl ester as white crystals, mp 110.5°–112.5° C.

EXAMPLE 13

Preparation of 1α-Acetoxy-24-deutero-25-hydroxycholesterol-3-Acetate

To a stirred, ice-cooled solution of 0.48 g (1.0 mmol) of cholesta-5,24-diene-1α,3β-diol diacetate in 15 ml of tetrahydrofuran was added 10 ml of water followed by 0.33 g (1.04 mmol) of mercuric acetate. After 3.5 hr., an additional 100 mg (0.3 mmol) was added. The reaction was left stirring overnight at room temperature and then was cooled in an ice bath. Solid sodium borodeuteride (100 mg) was added in 10 mg increments over a 15-min. period. After an additional 15 min., the reaction mixture was diluted with saturated sodium chloride and then extracted 4×25 ml with methylene chloride. The methylene chloride phases were washed with 2×50 ml of water, dried (Na$_2$SO$_4$), filtered and evaporated to give 508 mg of 1α-acetoxy-24-deutero-25-hydroxy-cholesterol-3-acetate as a viscous gum.

EXAMPLE 14

Preparation of 1α,3β-Diacetyloxychola-5,16,22-trien-24-oic Acid Methyl Ester

To a stirred solution of 0.13 ml (1.5 mmol) of methyl propiolate in 10 ml of dry methylene chloride (over 4 Å molecular sieves) under a nitrogen atmosphere was added 0.954 g (3.5 mmol) of aluminum tribromide. Immediately thereafter was added 398 mg (1 mmol) of Z-pregna-5,17(20)-diene-1α,3β-diol diacetate dissolved in 10 ml dry methylene chloride. The orange-colored solution was stirred for 15 min. A 2-ml sample was quenched with 5 ml of 10% aqueous potassium sodium tartrate salts. Analysis of the organic phase showed 20% of 1α,3β-diacetyloxychola-5,16,22-trien-24-oic acid methyl ester had formed (GC analysis).

EXAMPLE 15

Preparation of 1α,3β-Diacetyloxychola-5,16-dien-24-oic Acid Methyl Ester

To a stirred solution of 1.875 g (7 mmol) of aluminum tribromide in 10 ml of dry benzene (over 4 Å molecular sieves) under a nitrogen atmosphere was added 0.45 ml (5 mmol) of methyl acrylate. After 5 min., 0.08 ml (1 mmol) of pyridine was added, followed 5 min. later by 400 mg (1 mmol) of Z-pregna-5,17(20)-diene-1α,3β-diol diacetate dissolved in 10 ml dry benzene. The pale yellow solution was stirred for 1 hr. A 2-ml sample was quenched with 5 ml of 10% aqueous potassium sodium tartrate salts. Analysis of the organic phase showed 62% of 1α,3β-diacetyloxychola-5,16-dien-24-oic acid methyl ester had formed (GC analysis).

What is claimed is:

1. A process for the synthesis of chenodeoxycholic acid as characterized by the formula

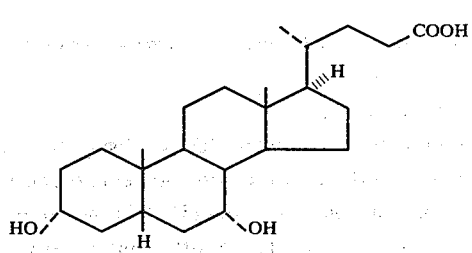

which process comprises the steps of (a) reacting a compound of the formula

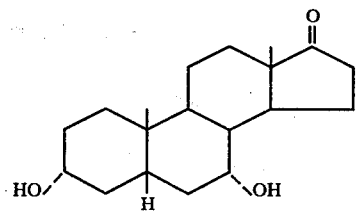

with an ethyltriphenylphosphonium halide in the presence of strong base to yield a compound of the formula

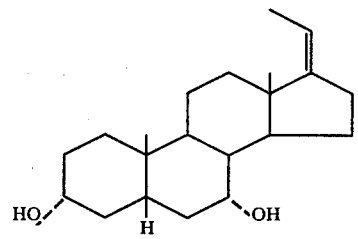

(b) reacting the reaction product of step (a) with an acylating agent in the presence of weak base at temperatures ranging from 0° to 150° C. so as to yield compounds of the formula

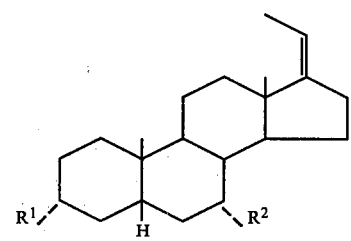

wherein $R^1$ and $R^2$ are acyloxy;

(c) reacting the reaction product of step (b) with an acrylic acid ester in the presence of Lewis acid catalysts selected from the group consisting of lower alkyl aluminum dihalides and aluminum trihalides in weak base in an inert solvent at temperatures ranging from −20° to 45° C. so as to yield a compound of the formula

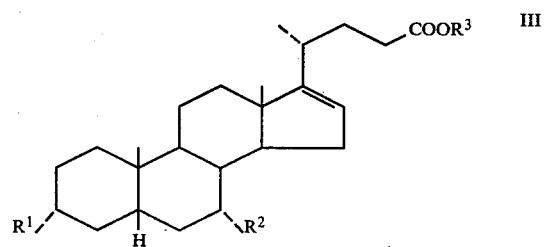

wherein $R^1$ and $R^2$ are acyloxy; and $R^3$ is lower alkyl;

(d) reacting the reaction product of step (c) with hydrogen in the presence of a conventional hydrogenation catalyst thereby reducing the $\Delta^{16}$ double bond so as to yield a compound of the formula

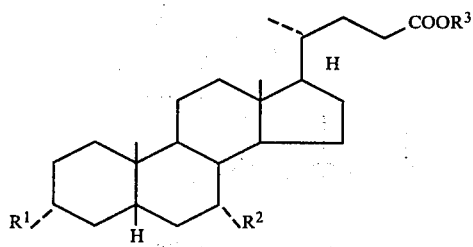

wherein $R^1$ and $R^2$ are acyloxy; and $R^3$ is lower alkyl;

(e) reacting the reaction product of step (d) with aqueous base at temperatures ranging from room temperature to reflux temperature so as to yield chenodeoxycholic acid as characterized by the formula

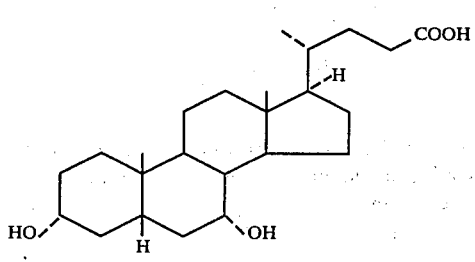

2. The process according to claim 1 wherein said Lewis acid is selected from the group consisting of ethylaluminum dichloride, aluminum tribromide in pyridine and aluminum chloride in pyridine.

3. The process according to claim 2 wherein said Lewis acid is aluminum chloride in pyridine.

4. The process according to claim 3 wherein said acylating agent is selected from the group consisting of lower alkyl carboxylic acid anhydrides and aromatic anhydrides.

5. The process according to claim 4 wherein said lower alkyl carboxylic acid anhydride is acetic anhydride.

6. The process according to claim 5 wherein said acrylic acid ester is methyl acrylate.

7. The process according to claim 6 wherein said conventional hydrogenation catalyst is selected from the group consisting of 5% platinum on charcoal, platinum oxide and Raney nickel.

8. The process according to claim 7 wherein said hydrogenation catalyst is 5% platinum on charcoal.

9. The process according to claim 8 wherein said aqueous base is potassium hydroxide.

10. A process for the synthesis of compounds of the formula

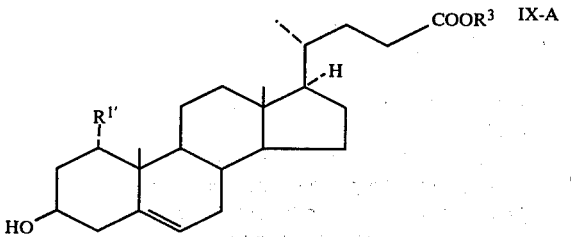

wherein $R^{1'}$ is hydrogen or hydroxy; and $R^3$ is lower alkyl, which comprises the steps of (a) reacting a compound of the formula

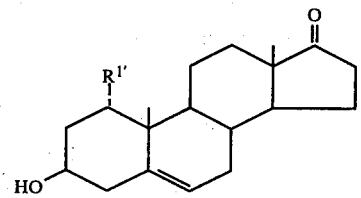

wherein $R^{1'}$ is hydrogen or hydroxy, with an ethyltriphenylphosphonium halide in the presence of strong base to yield a compound of the formula

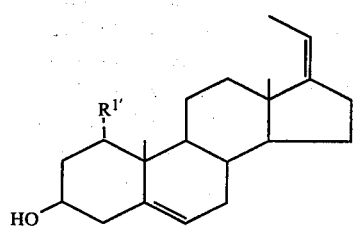

wherein $R^{1'}$ is hydrogen or hydroxy;

(b) reacting the reaction product of step (a) with acrylic acid esters in an inert solvent at temperatures ranging from $-20°$ to $45°$ C. in the presence of Lewis acids selected from the group consisting of lower alkyl aluminum dihalides and aluminum trihalides in weak base to yield compounds of the formula

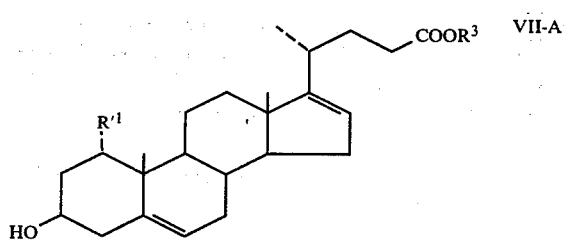

wherein $R^{1'}$ is hydrogen or hydroxy; and $R^3$ is lower alkyl, or, alternatively;

(c) reacting the reaction product of step (a) with propiolic acid esters in an inert solvent at temperatures ranging from $-20°$ to $45°$ C. in the presence of Lewis acids selected from the group consisting of lower alkyl aluminum dihalides and aluminum trihalides in weak base to yield compounds of the formula

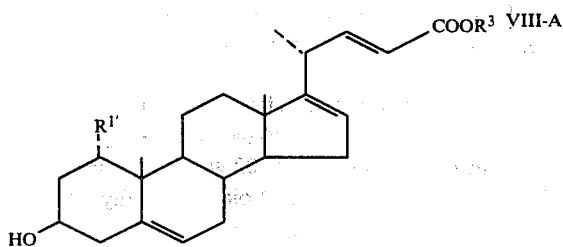

VIII-A wherein R$^{1'}$ is hydrogen or hydroxy;

(d) reacting the reaction product of step (a) or (b) with hydrogen in an inert solvent in the presence of a hydrogenation catalyst at temperatures ranging from 0° to 48° C. to yield compounds of the formula

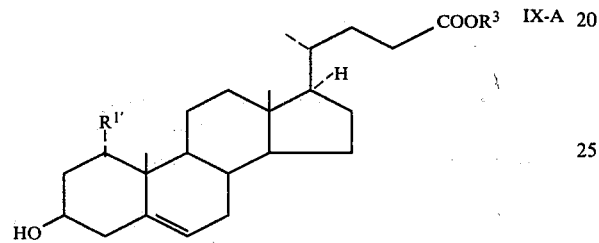

IX-A wherein R$^{1'}$ is hydrogen or hydroxy; and R$^3$ is lower alkyl.

11. A process for the synthesis of compounds of the formula

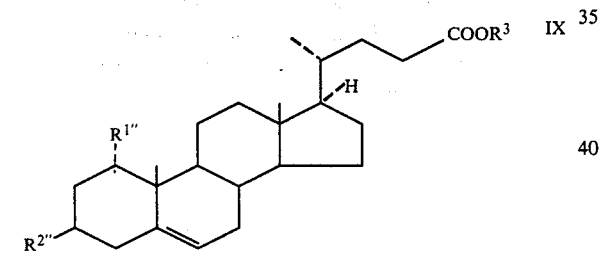

IX wherein R$^{1''}$ is hydrogen, hydroxy or acyloxy; and R$^{2''}$ is hydroxy or acyloxy, which comprises the steps of (a) reacting a compound of the formula

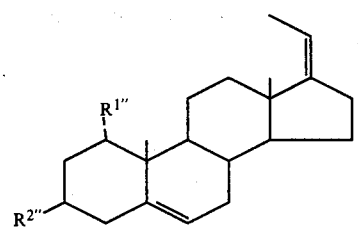

VI wherein R$^1$ is hydrogen, hydroxy or acyloxy; and R$^2$ is hydroxy or acyloxy, with acrylic acid esters in an inert solvent at temperatures ranging from −20° to 45° C. in the presence of Lewis acids selected from the group consisting of lower alkyl aluminum dihalides and aluminum trihalides in weak base to yield compounds of the formula

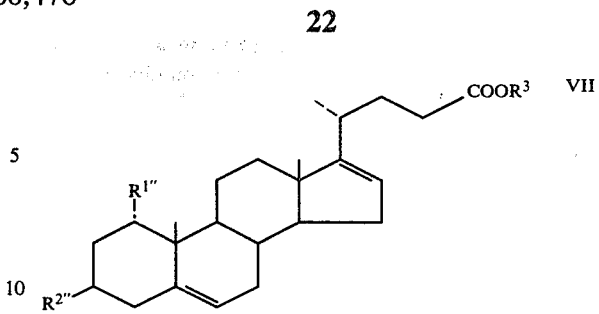

VII wherein R$^{1''}$ is hydrogen, hydroxy or acyloxy; R$^{2''}$ is hydroxy or acyloxy; and R$^3$ is lower alkyl; or, alternatively;

(b) reacting the reaction product of step (a) with propiolic acid esters in an inert solvent at temperatures ranging from −20° to 45° C. in the presence of Lewis acids selected from the group consisting of lower alkyl aluminum dihalides and aluminum trihalides in weak base to yield compounds of the formula

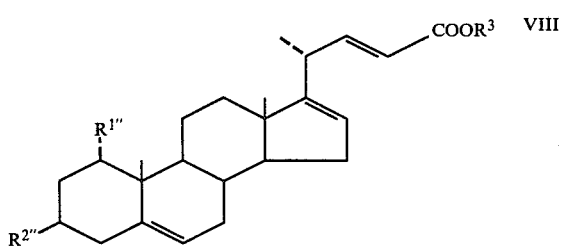

VIII wherein R$^{1''}$ is hydrogen, hydroxy or acyloxy; R$^{2''}$ is hydroxy or acyloxy; and R$^3$ is lower alkyl;

(c) reacting the reaction product from step (a) or (b) with hydrogen in an inert solvent in the presence of a hydrogenation catalyst at temperatures ranging from 0° to 40° C. to yield compounds of the formula

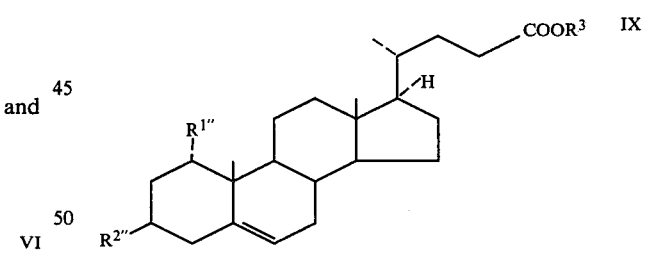

IX wherein R$^{1''}$ is hydrogen, hydroxy or acyloxy; R$^{2''}$ is hydroxy or acyloxy; and R$^3$ is lower alkyl.

12. The process according to claim 11 wherein said Lewis acid is selected from the group consisting of ethylaluminum dichloride, aluminum tribromide with pyridine and aluminum chloride with pyridine.

13. The process according to claim 12 wherein said Lewis acid is aluminum chloride with pyridine.

14. The process according to claim 13 wherein said acrylic acid ester is methyl acrylate.

15. The process according to claim 13 wherein said propiolic acid ester is methyl propiolate.

16. The process according to claim 14 or 15 wherein said hydrogenation catalyst is selected from the group consisting of 5% platinum on charcoal, platinum oxide and Raney nickel.

17. The process according to claim 16 wherein said hydrogenation catalyst is 5% platinum on charcoal.

18. The process according to claim 17 wherein said hydrogenation reaction is carried out at room temperature.

19. Compounds of the formula

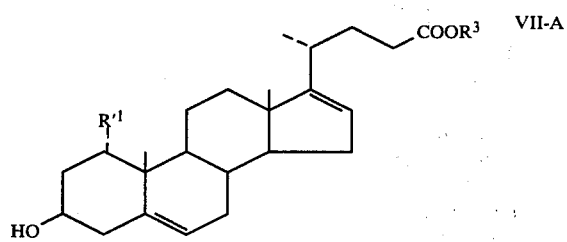

wherein $R^{1'}$ is hydrogen or hydroxy; and $R^3$ is lower alkyl.

20. The compound of claim 19 wherein $R^{1'}$ is hydrogen; and $R^3$ is lower alkyl.

21. The compound of claim 20 which is 3β-hydroxychola-5,16-dien-24-oic acid methyl ester.

22. The compound of claim 19 wherein $R^{1'}$ is hydroxy; and $R^3$ is lower alkyl.

23. The compound of claim 22 which is 1α,3β-dihydroxychola-5,16-dien-24-oic acid methyl ester.

24. Compounds of the formula

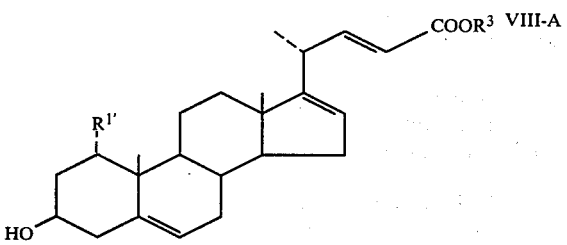

wherein $R^{1'}$ is hydrogen or hydroxy; and $R^3$ is lower alkyl.

25. The compound of claim 24 wherein $R^{1'}$ is hydrogen; and $R^3$ is lower alkyl.

26. The compound of claim 25 which is 3β-hydroxychola-5,16,22-trien-24-oic acid methyl ester.

27. The compound of claim 24 wherein $R^{1'}$ is hydroxy.

28. The compound of claim 27 which is 1α,3β-dihydroxychola-5,16,22-trien-24-oic acid methyl ester.

29. Compounds of the formula

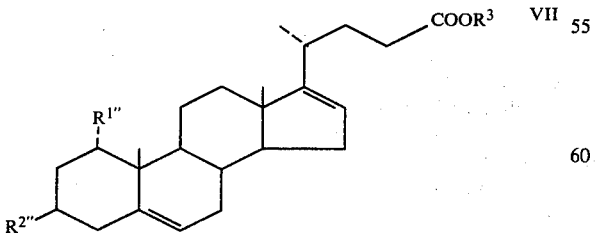

wherein $R^{1''}$ is hydrogen, hydroxy or acyloxy; $R^{2''}$ is hydroxy or acyloxy; and $R^3$ is lower alkyl.

30. The compound of claim 29 wherein $R^{1''}$ is hydrogen.

31. The compound of claim 30 which is 3β-acetyloxychola-5,16-dien-24-oic acid methyl ester.

32. The compound of claim 29 wherein $R^{1''}$ is acyloxy.

33. The compound of claim 32 which is 1α,3β-diacetyloxychola-5,16-dien-24-oic acid methyl ester.

34. The compound of claim 32 which is 1α-acetyloxy 3β-hydroxychola-5,16-dien-24-oic acid methyl ester.

35. Compounds of the formula

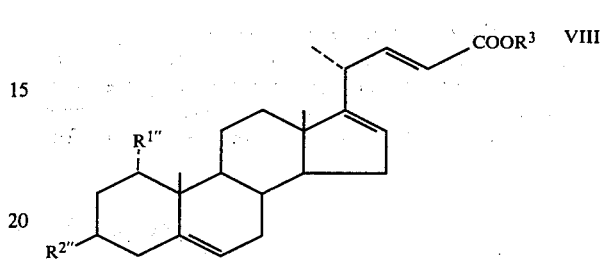

wherein $R^{1''}$ is hydrogen, hydroxy or acyloxy; $R^{2''}$ is hydroxy or acyloxy; and $R^3$ is lower alkyl.

36. The compound of claim 35 wherein $R^{1''}$ is hydrogen.

37. The compound of claim 36 which is 3β-acetyloxychola-5,16,22-trien-24-oic acid methyl ester.

38. The compound of claim 35 wherein $R^{1''}$ is acyloxy.

39. The compound of claim 38 which is 1α,3β-diacetyloxychola-5,16,22-trien-24-oic acid methyl ester.

40. The compound of claim 38 which is 1α-acetyloxy-3β-hydroxychola-5,16,22-trien-24-oic acid methyl ester.

41. (Z)-3α,5β,7α-pregn-17(20)-ene-3,7-diol as characterized by the formula

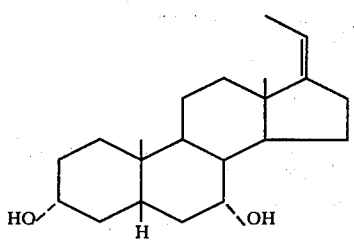

42. (Z)-3α,5β,7α-pregn-17(20)-ene-3,7-diol diacetate as characterized by the formula

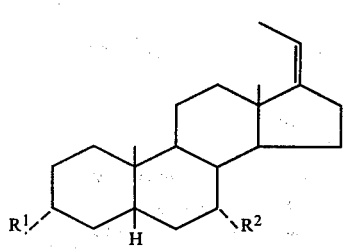

wherein $R^1$ and $R^2$ are acyloxy.

43. 3α,5β,7α-3,7-diacetyloxychol-16-en-24-oic acid methyl ester as characterized by the formula

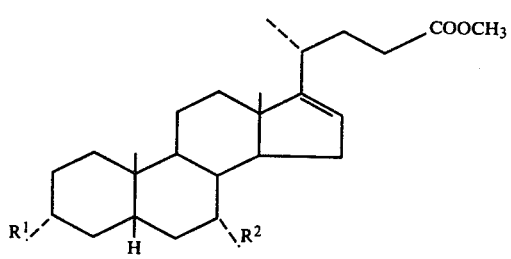
wherein R¹ and R² are acyloxy.
* * * * *